United States Patent
Negro

(10) Patent No.: US 6,288,400 B1
(45) Date of Patent: Sep. 11, 2001

(54) PORTABLE APPARATUS FOR THE MEASUREMENT OF ENVIRONMENTAL RADON AND THORON

(75) Inventor: Vincent C. Negro, New Hyde Park, NY (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/376,988

(22) Filed: Aug. 19, 1999

(51) Int. Cl.[7] ................................... G01N 27/66
(52) U.S. Cl. .................. 250/380; 250/382; 250/384; 250/255; 250/DIG. 2
(58) Field of Search .................. 250/380, 382, 250/384, 255, DIG. 2

(56) References Cited

U.S. PATENT DOCUMENTS 5,153,520 * 10/1992 Dumbeck .............................. 250/384
5,225,673 * 7/1993 Pressianov et al. ............ 250/DIG. 2

* cited by examiner

Primary Examiner—Constantine Hannaher
Assistant Examiner—Andrew Israel
(74) Attorney, Agent, or Firm—Bradley W. Smith; Mark P. Dvorscak; Virginia B. Caress

(57) ABSTRACT

The radometer is a portable instrument for the measurement of the concentration of atmospheric radon/thoron in a test area. A constant velocity pump pulls the air from the outside at a constant flow rate. If the air is too moist, some or all of the sample is passed through a desiccant filter prior to encountering an electrostatic filter. The electrostatic filter prevents any charged particles from entering the sampling chamber. Once the sample has entered the chamber, the progeny of the decay of radon/thoron are collected on a detector and measured. The measured data is compiled by a computer and displayed.

12 Claims, 3 Drawing Sheets

PORTABLE APPARATUS FOR THE MEASUREMENT OF ENVIRONMENTAL RADON AND THORON

STATEMENT REGARDING FEDERALLY SPONSORED RESEARCH AND DEVELOPMENT

The United States Government has rights in this invention pursuant to the employer-employee relationship of the U.S. Department of Energy and the inventor.

BACKGROUND OF THE INVENTION

1. Field of Invention

This invention, a Radometer, relates to an improved method for the measurement of environmental radon and thoron in homes and buildings. More particularly, this invention allows for the accurate measurement of radon and thoron using a portable, handheld electrical instrument and only a few minutes of time.

2. Description of Related Art

The measurement of radon and thoron in homes and buildings is important in determining the presence of a potential health hazard to persons occupying the structure. The concentration of radon is measured by counting the alpha particles resulting from the radioactive decay of radon, $^{222}Rn$, while the level of thoron is determined by counting the alpha particles from the radioactive decay of thoron, $^{220}Rn$. In the present invention four counting channels are used: two for radon and two for thoron.

An electrostatic filtering system is employed to insure that no positively charged particles enter the sampling chamber. In prior art, the filters were either in the form of a physical filter such as an open pore foam or an electrostatic filter. The use of a physical filter greatly increases the power consumption necessary to measure either the radon or the thoron.

Prior art often used natural air flow or manual fanning devices to move the air being sampled into a sampling chamber and then to the sensor. To provide for a more accurate measurement, the subject invention employs a constant velocity pump which provides a constant flow rate for the air moving into the sampling chamber.

Humidity causes the charged radioactive progeny to become neutrally charged which results in a lowering of the sensitivity of the instrument. Attempts to compensate for the humidity using a linear compensation method do not yield satisfactory results. The Radometer employs a nonlinear equation as a means of compensation together with a desiccator as is needed.

The Radometer measures radon and thoron by electrostatic collection of charged progeny on a solid state detector. A dual electrostatic field technique eliminates the need for a physical air filter and electric power draining pumps present in other radon measuring instruments. The Radometer allows accurate measurements to be made in 10 to 15 minutes or less.

To perform radon measurements in under 15 minutes requires alpha spectroscopy which the Radometer employs. This method resolves and measures the 6 MeV alpha particle that is emmitted as the radon progeny of $^{218}Po$ decay. Po-218 has a half life of 3 minutes which permits rapid measurement provided the instrument has adequate sensitivity. Using the dual electric field concept eliminates the need for filters or pumps since it insures that no electrically charged progeny can enter the measurement volume. This allows only the $^{218}Po$ that collects on the solid state detector as a result of the decay of the radon in the collected gas sample to be measured.

Another problem that is commonly encountered occurs when making measurements in an area of low radon concentration following measurements taken in an area having a high concentration of radon. Generally in prior art, this change in environment causes the detector to have a high background making it difficult to distinguish low concentration values. The Radometer employs software that incorporates exponential superposition which allows for the rapid determination of low concentration values subsequent to a high concentration measurement.

Thus, one objective of this invention is to provide an instrument for the measurement of the concentration of radon and thoron in the environmental atmosphere in twenty minutes or less.

Another objective of this invention is to provide an instrument which is lightweight and provides for a long operation life using standard batteries which are readily available such as D-cell.

Another objective of the invention is to provide an instrument with the flexibility to operate in many different environments with little difficulty.

Additional advantages, objects and novel features of the invention will become apparent to those skilled in the art upon examination of the following and by practice of the invention.

SUMMARY OF THE INVENTION

To achieve the foregoing and other advantages, this invention is an instrument to measure the concentration of radon and thoron by electrostatic collection of charged progeny on a detector. A dual electric field configuration eliminates the need physical sampling filters while the large volume of the sampling chamber results in a fast response time. An on-board computer records the data from the detector and corrects the data as needed prior to output. The sampling chamber has a volume of 6 liters.

BRIEF DESCRIPTION OF THE DRAWINGS

The present invention is illustrated in the accompanying drawings where.

DETAILED DESCRIPTION OF THE INVENTION

Figure 1:
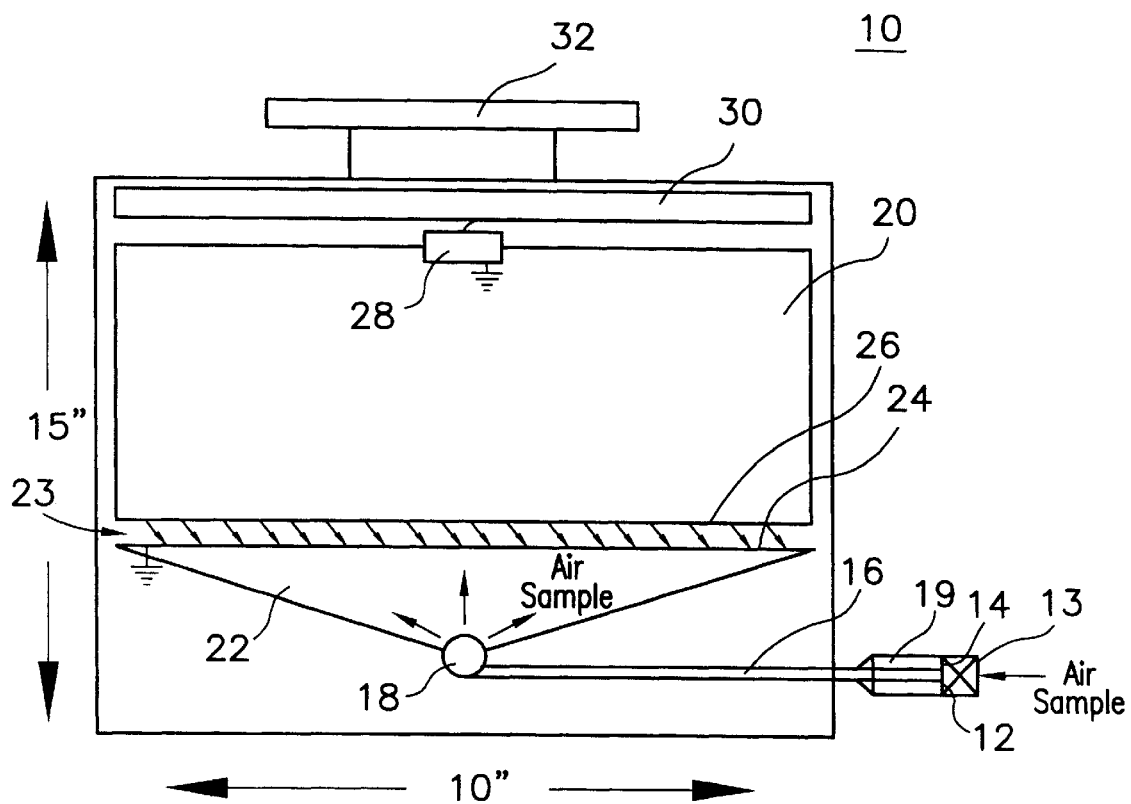
FIG. 1 is a schematic showing a cross section of the radometer.

FIG. 1 depicts a cross sectional schematic of the radometer 10. Air samples enter the radometer 10 via entrance ports 12, 14, or both depending on the water vapor content of the sample. If the water vapor content is not of concern, port 14 is completely closed by means of valve 13, and the sample enters through port 12 and passes unaltered directly through duct 16 to the intake of a constant velocity pump 18. If the water vapor content of sample is of great concern, port 12 is closed by means of valve 13, and the sample enters through port 14 where it is routed through a desiccant filter 19 to remove most of the water vapor prior to entering duct 16 leading to the constant velocity pump 18. The removal of the water vapor improves the sensitivity of the instrument, the Radometer. For cases in between, where only part of the water vapor needs to be removed, valve 13 is adjusted to route part of the air stream through port 12 and part through port 14. The proportion of the total air flow which flows through each port is dependent on the amount of water vapor which needs to be removed to retain the desired instrument sensitivity. The constant velocity pump 18 is used so that the air sample travels at a constant flow rate to the sample chamber 20. Maintaining a constant flow rate is important for measuring thoron due to its short half-life. After exiting the constant velocity pump or pump 18, the air sample enters a diffusion duct 22 and flows to a perforated cap 24. The perforated cap 24 is separated from the perforated base 26 of the sample chamber 20 by an air gap of approximately one inch. The sample chamber 20 including its base 26 is at a voltage potential of 3000 volts with respect to ground. The cap 24 of the diffusion duct 22 is grounded resulting in it having a potential relative to the base 26 of approximately 0 volts. The voltage differential across the air gap between the base 26 and the cap 24 creates an electronic filter 23 which prevents any charged progeny from the parent radon/thoron gas from entering the sample chamber 20. This type filter is effective since it prevents all charged particles from entering the sampling chamber 20.

Once the air sample is in the 6 liter sample chamber 20, the radon/thoron gas undergoes a radioactive decay to form the progeny $^{214}$Po and $^{218}$Po for radon and $^{216}$Po and $^{212}$Po for thoron. A detector 28 is positioned so that its detection surface is interior to the sample chamber. The electrical potential of the detector 28 is at ground (0V) potential so that a second electrical field is setup this one interior to the sample chamber. Since the radon/ithoron progeny are 80% positively charged, a collection mechanism is established by which these charged progeny migrate from the interior volume of the sample chamber to the detector 28. Neutral progeny that enter the sample chamber and undergo further decay will also be collected but not as Po-216 or Po-218. The use of a 6 liter sampling chamber results in improved measurement sensitivity when compared to smaller chambers. Further increases in sensitivity can be attained by increasing the volume of the sample chamber. In most cases, the voltage potential of the sample chamber relative to the detector is also increased as the size of the sample chamber is increased.

The electronics used to record the counts as detected by the detector 28 is housed in the electronics compartment 30. A four channel electronic system is used to count the radon/thoron progeny. These channels register alpha counts from $^{218}$Po with an energy of 6.0 MeV and $^{214}$Po with an energy of 7.7 MeV in the radon decay chain, and from $^{216}$Po with an energy of 6.8 MeV and $^{212}$Po with an energy of 8.8 MeV in the thoron decay chain. Thoron also produces $^{212}$Bi with an alpha energy of 6.06 MeV. This cannot be resolved from the $^{218}$Po alpha at 6.0 MeV; however, $^{212}$Po and $^{212}$Bi are produced in an approximate 2 to 1 ratio which permits a correction to be made. For example, if 50 counts are registered on the $^{212}$Po channel then half or 25 must be subtracted from the $^{218}$Po channel to correct for the contribution of $^{212}$Bi. This correction is made by an on board computer. The power source for the system is contained in the handle 32 of the radometer. In the current embodiment, three D-cell flashlight batteries are used 92, FIG. 2. The use of the three batteries will power the radometer for several days.

Figure 2:
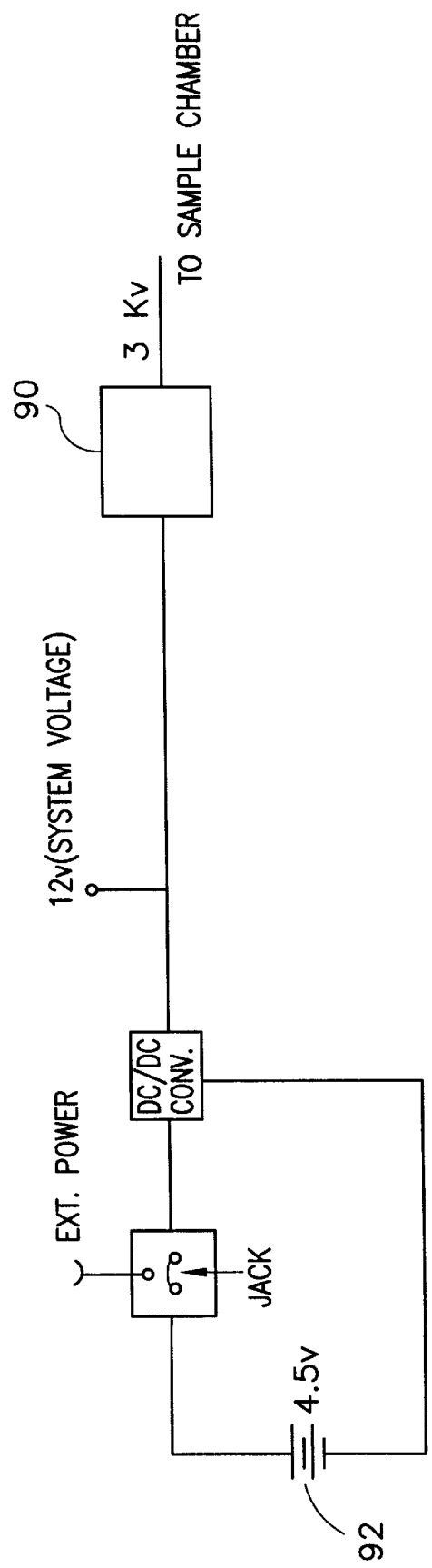
FIG. 2 is a schematic of the power supply system.
Figure 3:
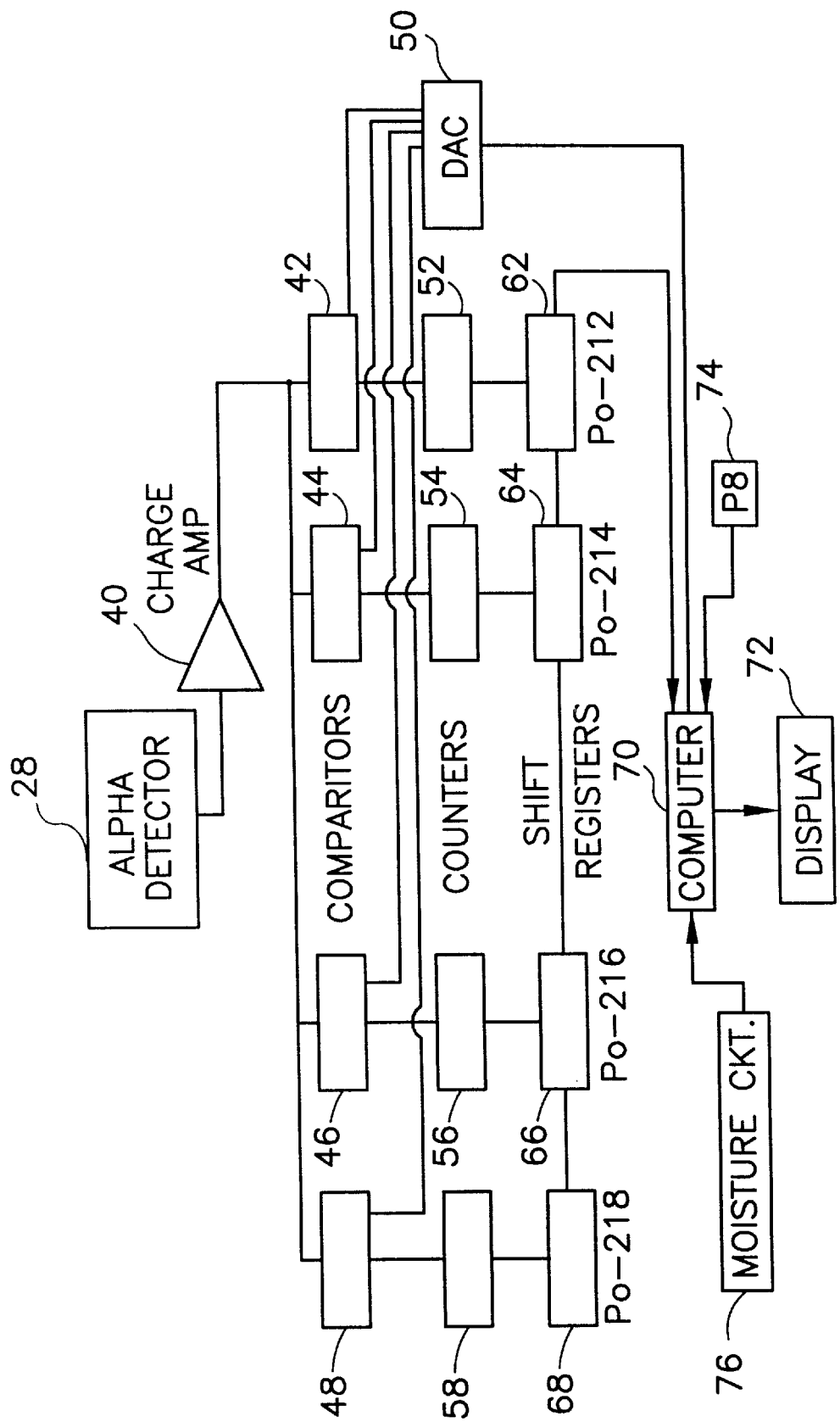
FIG. 3 illustrates the electronics which collect, analyze and output the data.

As noted, with the decay of the radon/thoron gas, the charged progeny are attracted to the detector 28 by the electric field set up by the 3 Kv voltage source 50, FIG. 2, and the grounded detector 28. Once on the detector, the progeny further decay by alpha emission. The alpha emission causes a small electric pulse in the detector which is coupled to an amplifier 40. The pulse from the amplifier is routed to four comparators 42,44,46,and 48. This enables the two alpha energies from the decay of the radon gas (Rn-222), $^{218}$Po and $^{214}$Po to be separated and counted. It, also, allows the two energies from the decay of thoron gas (Rn-220), $^{216}$Po and $^{212}$Po to be separated and counted. The output of each of the comparators is as follows: comparator 42 measures $^{212}$Po, comparator 44 measures $^{212}$Po +$^{214}$Po, comparator 46 measures $^{212}$Po +$^{214}$Po +$^{216}$Po, and comparator 48 measures $^{212}$Po +$^{214}$Po +$^{216}$Po +$^{218}$Po. Individual counts are obtained by subtracting the count from one comparator from another to obtain the desired result. For example, the count for $^{216}$Po is obtained by subtracting the reading of comparator 46 from 44. The pulses coming out of each of the four comparators are counted by counters which are paired one on one with each comparator. Counters 52, 54, 56, and 58 are paired with comparators 42, 44, 46, and 48 respectively. Once a second, the information in each of the counters is transferred to shift registers 62, 64, 66, and 68 where it is shifted as one long 32 bit binary number to the computer 70. The computer 70 then separates the 32 bits into four counts, analyzes the data and displays the information on the display 72 in pCi/l. The quad digital analog converter 50 combines with the computer 70 to automatically set all adjustments to the Radometer 10. A radioactive source $^{210}$Po is used to calibrate the Radometer. The $^{210}$Po is deposited on and remains on the detector 28 and produces alpha particles having an energy of 5.3 Mev. This energy level is well below the 6.0 Mev energy level of $^{218}$Po which has the lowest energy level of the isotopes of interest. In normal operation, controlled by the depressing and releasing push-button 74, the $^{210}$Po isotope is not registered, but when the operator desires to calibrate the instrument the push-button is held in the depressed position until a signal appears on the display 72 indicating that the instrument, Radometer, is in the calibration mode. Instructions are then transferred from the computer to the DAC 50 to set Comparator 48 to count the $^{210}$Po source in addition to the other four isotopes. The calibration operation completely checks all of the electronics in the instrument from the detector 28 to the display 72.

A humidity/temperature sensor 76 is coupled to the computer 70 and is used to determine the moisture content of the air sample. The instrument was tested over a range to temperatures/humidity, to develop a data base. This data base was used with a nonlinear fitting technique to develop a set of equations to determine the sensitivity of the instrument at various atmospheric conditions of temperature and humidity. These equations were programmed into the instrument's computer 70. Using these equations, the instrument displays its sensitivity on the display panel 72. When high humidity lowers the sensitivity of the instrument below the acceptable level, the operator can raise the sensitivity by letting the air sample flow through the desiccant cartridge 19 to dry the sample. The constant velocity pump 18 insures the increase pressure drop due to the cartridge 19 has no effect on flow rate.

To perform a radon concentration measurement in 10 to 15 minutes requires alpha spectroscopy which resolves and measures the 6 MeV alpha that is emitted as the radon progeny $^{218}$Po decays. Po-218 has a half life of 3 minutes which permits a rapid measurement provided the instrument has adequate sensitivity. The sensitivity of the Radometer is typically 3 cpm/pCi/l. Radon has a higher energy alpha that results from the decay of $^{214}$Po which has an energy of 7.8 MeV, but is half life is almost an hour making its measurement unsuitable for "sniffer" application. As noted above, the instrument measures both Po-218 and Po-214 but only uses the $^{218}$Po to calculate the radon concentration. Since a dual electric field is used, the electrostatic filter 23 and the field internal to the sample chamber, this insures that no electrically charged progeny can enter the sample chamber 20; thus, the only $^{218}$Po that can be collected on the solid state detector 28 must originate in the sample chamber 20.

In cases where measurements are taken first in an area of high radon/thoron concentration and then in areas of low radon/thoron concentration a software program in the computer 70 employs an exponential superposition technique to correct for the high background brought on by the high concentration of radon in the initial sampling.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

The embodiment of this invention in which an exclusive property or privilege is claimed is defined as follows:

1. An instrument for the measurement of the concentration of radon or thoron at a specific site comprising:
    a sample intake means for allowing the passage of an air sample taken from an exterior location to a connecting tube interior to the instrument;
    an air sample pump having an inlet port and an exit port where said inlet port is connected to said intake means by said connecting tube;
    a diffuser duct having a coupling port on one end and a perforated cap on the other end of said duct where said coupling port mates with said exit port of said pump to form a confined path for said air sample as it leaves said pump and moves to said cap;
    a sample chamber having a perforated base, continuous sides and a top where said sample chamber confines said air sample;
    a detection device where said detection device is mounted on said top of said sample chamber and where said detection device is oriented so that it s detection surface is exposed to an interior volume of said sample chamber;
    a counting means for counting a group of radon/thoron progeny as detected by said detector and transferring this data to a computer for analysis and output to a display mechanism;
    a humidity compensation means for detecting a humid condition which would compromise the instruments sensitivity where said humidity compensation means is coupled to said computer;
    a power source means for supplying electrical power to the instrument.

2. The apparatus of claim 1 where said sample intake means has a first entry port for air with a low humidity as determined by said humidity compensation means and a second entry port for air with a high humidity level as determined by said humidity compensation means and where if said second entry port is used said sample passes through a desiccant filter prior to entering said connecting tube.

3. The apparatus of claim 1 where said air sample pump is a constant velocity pump which moves the sample through the connecting tube at a constant flow rate.

4. The apparatus of claim 1 wherein said cap of said diffuser duct is electrically grounded.

5. The apparatus of claim 1 where said detection device is electrically grounded.

6. The apparatus of claim 1 where said sample chamber has a volume of approximately 6 liters and is at an electrical potential of 3,000 volts.

7. The apparatus of claim 1 wherein said detector detects Po-212, Po-214, Po-216, and Po-218, progeny of the radioactive decay of radon and thoron.

8. The apparatus of claim 7 wherein said counting means includes an amplifier coupled to said detector and to a series of four comparitors each of which is individually linked to a counter which in turn is linked to a shift register to form a series of four counting units where the result of these combinations is to count respective progeny associated with radon/thoron's decay.

9. The apparatus of claim 8 wherein each of said counting units are serially linked through said shift registers and then a composite signal representing a concentration of the progeny is transferred to said computer for analysis and where the results of said analysis outputs to said display.

10. The apparatus of claim 9 wherein a quad digital/analog converter is coupled to a reference source, said computer and to each of said comparitors where said digital/analog converter together with a radioactive Po-210 source which is permanently deposited on said detector allows the instrument to be self calibrated and to fully check all of the electronics of said instrument.

11. The apparatus of claim 1 where said power source means includes a main power source, three D-cell batteries housed in a handle attached to an exterior casing of the instrument, and a back-up battery coupled to said computer which maintains a program in said computer and stored data when said main power source is off-line.

12. The apparatus of claim 1 where said humidity compensation means includes a humidity and temperature sensor a data stream from which inputs to said computer which employs a series of nonlinear equations programmed in said computer to correlated a sensitivity reading for the instrument based on said data stream and where said sensitivity outputs to said display device.

* * * * *